United States Patent
Snyder et al.

(10) Patent No.: US 11,969,401 B2
(45) Date of Patent: Apr. 30, 2024

(54) COMPOSITIONS AND METHODS FOR TREATING OR LIMITING DEVELOPMENT OF AGE-RELATED MACULAR DEGENERATION

(71) Applicant: Arizona Board of Regents on Behalf of The University of Arizona, Tucson, AZ (US)

(72) Inventors: Robert Snyder, Tucson, AZ (US); Brian McKay, Tucson, AZ (US)

(73) Assignee: ARIZONA BOARD OF REGENTS ON BEHALF OF THE UNIVERSITY OF ARIZONA, Tucson, AZ (US)

(*) Notice: Subject to any disclaimer, the term of this patent is extended or adjusted under 35 U.S.C. 154(b) by 231 days.

(21) Appl. No.: 17/427,370

(22) PCT Filed: Jan. 30, 2020

(86) PCT No.: PCT/US2020/015860
§ 371 (c)(1),
(2) Date: Jul. 30, 2021

(87) PCT Pub. No.: WO2020/160256
PCT Pub. Date: Aug. 6, 2020

(65) Prior Publication Data
US 2022/0023245 A1     Jan. 27, 2022

Related U.S. Application Data

(60) Provisional application No. 62/799,444, filed on Jan. 31, 2019.

(51) Int. Cl.
| | |
|---|---|
| A61K 31/198 | (2006.01) |
| A61K 31/165 | (2006.01) |
| A61K 31/222 | (2006.01) |
| A61K 31/343 | (2006.01) |
| A61K 31/4045 | (2006.01) |
| A61K 38/05 | (2006.01) |
| A61K 38/06 | (2006.01) |
| A61K 47/54 | (2017.01) |

(52) U.S. Cl.
CPC .......... *A61K 31/198* (2013.01); *A61K 31/165* (2013.01); *A61K 31/222* (2013.01); *A61K 31/343* (2013.01); *A61K 31/4045* (2013.01); *A61K 38/05* (2013.01); *A61K 38/06* (2013.01); *A61K 47/554* (2017.08)

(58) Field of Classification Search
CPC .. A61K 31/198; A61K 47/554; A61K 31/165; A61K 31/222; A61K 31/343; A61K 31/4045; A61K 38/05; A61K 38/06
See application file for complete search history.

(56) References Cited

U.S. PATENT DOCUMENTS

| | | |
|---|---|---|
| 3,803,120 A | 4/1974 | Felix |
| 3,891,696 A | 6/1975 | Bodor |
| 4,035,507 A | 7/1977 | Bodor |
| 4,065,566 A | 12/1977 | Bodor |
| 4,663,349 A | 5/1987 | Repta |
| 4,771,073 A | 9/1988 | Repta |
| 4,873,263 A | 10/1989 | Repta |
| 5,345,885 A | 9/1994 | Yoshino |
| 5,686,423 A | 11/1997 | Wang |
| 2002/0151526 A1 | 10/2002 | Gallop |
| 2006/0025385 A1 | 2/2006 | Atlas |
| 2015/0142085 A1 | 5/2015 | Baron |
| 2016/0015665 A1 | 1/2016 | McKay |
| 2018/0104275 A1* | 4/2018 | Ryazanov ............. A61K 45/06 |

FOREIGN PATENT DOCUMENTS

| | | |
|---|---|---|
| WO | 1997016181 | 5/1997 |
| WO | 2002028882 | 4/2002 |
| WO | 2004069146 | 8/2004 |
| WO | WO-2009129497 A2 * | 10/2009 ............. A61K 31/00 |

OTHER PUBLICATIONS

Naskar et al (J Pineal Res. Apr. 2015 vol. 58. No. 3: pp. 262-274). (Year: 2015).*
Zaitone et al (Pharmaceutical Reports 2013 vol. 65, pp. 1213-1226). (Year: 2013).*
Brilliant et al (The American Journal of Medicine 2016 vol. 129: pp. 292-298). (Year: 2016).*
Shallenberger (Townsend Letter 427: 50(8); published Feb.-Mar. 2019). (Year: 2019).*
Rabin PhD Dissertation (Albany Medical College, 2007). (Year: 2007).*
Nutt, et al., "Response to Levodopa Treatment in Dopa-Responsive Dystonia", Arch Neurol., 58(6):905-910 (2001).
Spinelli, "Quest to End Macular Degeneration Continues With $1.7M Grant", UANews. UA Health Sciences., retrieved from webpage <http://www.arizona.edu>, Jun. 26, 2017, retrieved from internet < https://news.arizona.edu/story/quest-end-macular-degeneration-continues-17m-grant>, retrieved Oct. 3, 2022.
Yi, et al., "Effects of Melatonin in Age-Related Macular Degeneration", Ann. NY Acad. Sci., 1057:384-92 (2005). Abstract.

* cited by examiner

*Primary Examiner* — Catherine S Hibbert
(74) *Attorney, Agent, or Firm* — PABST PATENT GROUP LLP (57) ABSTRACT

The disclosure provides methods for treating or limiting development age-related macular degeneration, comprising (a) a GPR143 receptor agonist, including but not limited to L-DOPA, L-DOPA analogues, or a pharmaceutically acceptable salt thereof, and (b) melatonin, a melatonin analogue, or a pharmaceutically acceptable salt thereof, and related compositions.

17 Claims, 1 Drawing Sheet

COMPOSITIONS AND METHODS FOR TREATING OR LIMITING DEVELOPMENT OF AGE-RELATED MACULAR DEGENERATION

CROSS-REFERENCE TO RELATED APPLICATIONS

This application is a National Phase application under 35 U.S.C. § 371 of PCT/US2020/015860, filed Jan. 30, 2020, which claims priority to U.S. Provisional Patent Application Ser. No. 62/799,444, filed Jan. 31, 2019, incorporated by reference herein in their entirety.

STATEMENT REGARDING FEDERALLY SPONSORED RESEARCH OR DEVELOPMENT

This invention was made with government support under Grant No. R01 EY026544 awarded by National Institutes of Health. The government has certain rights in the invention.

BACKGROUND

Current treatments for age-related macular degeneration (AMD) are limited to repeated intraocular injections of antibodies or proteins that inhibit vascular endothelial growth factor activity, and these treatments are limited to the roughly 10% of individuals with wet AMD. Furthermore, repeated intraocular injections are expensive, painful, and lead to significant risk of infection. Thus, improved compositions and methods are needed for treating AMD.

SUMMARY

In a first aspect, the disclosure provides pharmaceutical compositions comprising:
  (a) a GPR143 receptor agonist, including but not limited to L-DOPA, L-DOPA analogues, or a pharmaceutically acceptable salt thereof;
  (b) melatonin, a melatonin analogue, or a pharmaceutically acceptable salt thereof; and
  (c) a pharmaceutically acceptable carrier.

In one embodiment, the composition comprises L-DOPA or a pharmaceutically acceptable salt thereof. In another embodiment, the composition comprises an L-DOPA prodrug, or a pharmaceutically acceptable salt thereof, including but not limited to an L-DOPA ester, a bile acid conjugate of L-DOPA, a di- or tri-peptide L-DOPA analogue, an amide L-DOPA analogue, or a pharmaceutically acceptable salt thereof.

In another embodiment, the composition comprises melatonin, or a pharmaceutically acceptable salt thereof. In another embodiment, the composition comprises a melatonin analogue, including but not limited to ramelteon, agomelatine, tasimelteon, or a pharmaceutically acceptable salt thereof.

In a further embodiment, the composition further comprises carbidopa or a pharmaceutically acceptable salt thereof.

In a further embodiment, the composition may be formulated as an oral dosage form or as eye drops. The composition may be provided as a pharmaceutical or a nutraceutical.

In a second aspect, the disclosure provides methods for treating or limiting development of AMD, comprising administering to a subject in need thereof an amount effective to treat or limit development of AMD of:
  (a) a GPR143 receptor agonist;
  (b) melatonin, a melatonin analogue, or a pharmaceutically acceptable salt thereof.

In one embodiment, the GPR143 receptor agonist comprises L-DOPA, an L-DOPA analogue, or a pharmaceutically acceptable salt thereof.

In one embodiment, the administering may be done in the evening 2 hours or less before the subject goes to bed; in another embodiment, the administering may be done in the evening 1 hour or less before the subject goes to bed. In a further embodiment, the administering is done once per day. In another embodiment, the administering may comprise administering the composition of any embodiment or combination of embodiments of the first aspect of the disclosure.

In one embodiment, the administering may comprise oral administering or administering by eye drops. In another embodiment, the method may be for treating AMD; in various such embodiments, the subject may have wet AMD or dry AMD. In a further embodiment, the method may be for limiting development of AMD, wherein the subject has one or more risk factors for AMD, including but not limited to drusen deposits, lipofuscin deposits, or pseudodrusen (RPD) deposits. In a further embodiment, the method may further comprise treating the subject with light therapy the morning following the administering.

DETAILED DESCRIPTION

All references cited are herein incorporated by reference in their entirety.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, CA), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, CA), *Culture of Animal Cells: A Manual of Basic Technique*, $2^{nd}$ Ed. (R. I. Freshney, 1987. Liss, Inc. New York, NY), *Gene Transfer and Expression Protocols*, pp. 109-128, ed. E. J. Murray, The Humana Press Inc., Clifton, N.J.), and the Ambion 1998 Catalog (Ambion, Austin, TX).

As used herein, the singular forms "a", "an" and "the" include plural referents unless the context clearly dictates otherwise. All embodiments may be combined unless the context clearly indicates otherwise.

In a first aspect, the present disclosure provides pharmaceutical composition comprising:
  (a) a GPR143 agonist, including but not limited to L-DOPA, an L-DOPA analogue, or a pharmaceutically acceptable salt thereof,
  (b) melatonin, a melatonin analogue, or a pharmaceutically acceptable salt thereof: and
  (c) a pharmaceutically acceptable carrier.

As shown in the examples that follow, the inventors have demonstrated that circadian agents alter retinal pigment epithelial (RPE) cell VEGF expression in a rhythmic manner, with dopamine receptors increasing RPE VEGF secretion, while melatonin and GPR143 agonists exemplified by L-DOPA antagonize dopamine effects, and thus that combining GPR143 agonists and melatonin induce RPE cells into a circadian rhythm that controls VEGF expression (a key contributor to AMD development). While not being bound by any specific mechanism of action, the compositions and methods of the disclosure may serve to entrain or reset key retinal functions to the daily light cycle so that the generation, release, phagocytosis, and processing of spent photoreceptor outer segments and handling of photo oxidized cellular material is coordinated with the metabolic functions of the retinal pigment epithelial cells, thus reducing the risk for or delay the progression of macular degeneration.

Thus, the pharmaceutical compositions are suitable, for example to treat or limit development of age-related macular degeneration, and can be used in the methods of the disclosure. Thus, in one embodiment the GPR143 agonist such as L-DOPA, L-DOPA analogue, melatonin, and/or melatonin analogue are present in an amount effective to treat or limit development of age-related macular degeneration (AMD) (each alone, or in combination).

In one embodiment, the composition comprises melatonin, or a pharmaceutically acceptable salt thereof. Melatonin is a hormone produced by the pineal gland, and is available from many commercial suppliers. Melatonin has the structure shown below.

In another embodiment, the composition comprises a melatonin analogue (i.e.: an agonist of the melatonin receptor), or a pharmaceutically acceptable salt thereof. Any suitable melatonin analogue may be used in the compositions of the disclosure, including but not limited to ramelteon (available from Takeda), agomelatine (available from Servier), and tasimelteon (available from Vanda Pharmaceuticals). The compositions of any embodiment may include both melatonin and one or more melatonin analogue, or pharmaceutically acceptable salts thereof.

In another embodiment, the composition comprises L-DOPA or a pharmaceutically acceptable salt thereof. L-DOPA is [2-amino-3-(3,4-dihydroxyphenyl)propanoic acid], and has the following structure.

L-DOPA stimulates the OA1 (GPR143) receptor to up-regulate PEDF activity, and is commercially available from a number of sources.

In another embodiment, the composition comprises an L-DOPA analogue, or a pharmaceutically acceptable salt thereof. As used herein, "L-DOPA analogues" are those L-DOPA variants that retain GPR143-stimulatory activity, including L-DOPA prodrugs, of which many are known in the art: exemplary such analogues are disclosed below. While not being bound by a specific mechanism of action, the inventor believes that L-DOPA binding to GPR143 involves two sites of binding, one involving one or both hydroxyl groups, and one involving the carboxylic acid group. In one embodiment, the L-DOPA analogues are L-DOPA prodrugs that are metabolized to L-DOPA after administration (and generally prior to binding to GPR143 on the cell surface), and thus are expected to retain GPR143-stimulatory activity. In another embodiment, one or both hydroxyl group and/or the carboxyl group can be substituted to produce various analogues (prodrug or otherwise) for use in the methods of the disclosure.

In another embodiment, the L-DOPA analogues comprise L-DOPA esters Exemplary L-DOPA esters, and methods for preparing them, are disclosed in WO/1997/016181; U.S. Pat. No. 4,663,349: U.S. Pat. Nos. 4,873,263; 4,873,263; 5,345,885, and 4,771,073. In various embodiments, the L-DOPA ester is selected from the group consisting of L-DOPA methyl ester, L-DOPA butyl ester, L-DOPA pentyl ester, L-DOPA cyclohexyl ester. L-DOPA benzyl ester, and L-DOPA ethyl ester. In various further embodiments, the L-DOPA esters are selected from the alkyl, aryl and substituted and unsubstituted aralkyl esters of L-DOPA. Synthetic processes for preparing the esters of L-DOPA and the salts thereof are known, for example, in U.S. Pat. Nos. 3,891,696; 4,035,507; and 5,354,885; and Journal of Pharmaceutical Sciences, 62, p. 510 (1973), each incorporated by reference herein in their entirety.

In another embodiment, the L-DOPA analogues comprise bile acid conjugates as are known in the art. Exemplary L-DOPA bile acid conjugates, and methods for preparing them, are disclosed in WO/2002/028882 and US20020151526. Upon oral administration, these prodrugs are cleaved within the enterohepatic system to release the parent drug and/or an active metabolite from the bile acid into the systemic circulation. Significantly, only a fraction (typically <50%)<50%) of the prodrug is cleaved during each pass through the enterohepatic cycle. Thus, the enterohepatic circulation serves as a reservoir of the drug enabling sustained systemic drug levels to be achieved. Naturally occurring bile acids such as cholic acid, chenodeoxycholic acid, ursodeoxycholic acid, deoxycholic acid, ursocholic acid and lithocholic acid may be used. The site of conjugation of these bile acids to L-DOPA or other L-DOPA analogue may be via the 3-hydroxy group or the C-24 carboxyl moiety. Optionally, cleavable linker functionality may be introduced between the drug and the bile acid and this linker may be selected.

In another embodiment, the L-DOPA analogues comprise di or tri-peptide derivatives. Exemplary L-DOPA di- or tri-peptide analogues, and methods for preparing them, are disclosed in U.S. Pat. Nos. 3,803,120 and 5,686,423. Oral absorption of the di- and tri-peptide L-DOPA prodrugs show high oral bioavailability with some compounds having the plasma concentration 60-100 fold higher than that of L-dopa.

In another embodiment, the L-DOPA analogues comprise amine prodrugs as are known in the art. Exemplary L-DOPA amine analogues, and methods for preparing them, are disclosed in US20060025385 and WO/2004/069146. In one embodiment, such L-DOPA amine analogues are represented by wherein *C denotes a chiral carbon;

R1, R2, R3 and R4 are each independently selected from the group consisting of hydrogen, alkyl having 1-30 carbon atoms, alkenyl having 1-30 carbon atoms, alkynyl having 1-30 carbon atoms, cycloalkyl, aryl, O-carboxy, C-carboxy, carbonyl, thiocarbonyl, O-carbamyl, 0-thiocarbamyl and a fatty acid acyl, or, alternatively. R1 and R2 and/or R3 and R4 form a five- or six-membered ring; and

R5 and R6 are each independently selected from the group consisting of hydrogen, alkyl, cycloalkyl, aryl and phosphonyl, or a pharmaceutically acceptable salt thereof.

Exemplary L-DOPA amine analogues include: compounds wherein R5 and R6 are each hydrogen; compounds wherein R1 and R2 are each hydrogen: compounds wherein R3 and R4 are each hydrogen; compounds wherein at least one of R1, R2, R3 and R4, preferably R3 and/or R4 is carbonyl, e.g., acetyl. Additional compounds according to the present disclosure include compounds wherein at least one of R1, R2, R3 and R4 is an alkyl, alkenyl or alkynyl having 1-30 carbon atoms, or, alternatively, at least one of R1, R2. R3 and R4 is a fatty acid acyl, derived from, for example, myristic acid, lauric acid, palmitic acid, stearic acid, oleic acid, arachidonic acid, linoleic acid or linolenic acid. Further preferred examples of L-DOPA amine analogues according to the present embodiments include α-amino-3,4-dihydroxy-benzenepropanamide. α-N-acetyl-3,4-dihydroxy-benzenepropanamide and pharmaceutically acceptable salts thereof.

In a further preferred embodiment, L-DOPA prodrugs for use in the present disclosure, and methods for their synthesis, are disclosed in U.S. Pat. Nos. 4,065,566 and 4,035,507 and are represented by the formula wherein each R is independently selected from the group consisting of a hydrogen atom, an acyl group, a group, a —CO-pyridyl group, and a —CO—R3 group, wherein R3 represents the residue of any N,N—C1-C2 dialkylamino acid or a C4-C6 cycloalkylamino acid wherein R1 represents a member selected from the group consisting of a hydroxyl group and a —OM group, wherein M is an alkali metal (Na, K, etc.) or an ammonium ion; and wherein R2 represents a member selected from the group consisting of a group, a —CO-pyridyl group, and a —CO—R3 group, wherein R3 represents the residue of any N,N—(C1-C2)-dialkylamino acid or a C4-C6-cycloalkylamino acid Further L-DOPA prodrugs for use in the present disclosure, and methods for their synthesis, disclosed in U.S. Pat. Nos. 4,065,566 and 4,035,507 are represented by the formula wherein R represents an acyl group; wherein R2 represents a hydrogen atom; and wherein R1 represents a —NHCH (R4)COOR5 group, wherein R4 represents the residue of any naturally occurring amino acid, and wherein R5 represents a member selected from the group consisting of a hydrogen atom, a C1-C5 alkyl group (e.g., methyl, ethyl, propyl, butyl, pentyl), and a C1-C5 alkylaryl group (e.g., —$CH_2$—$C_6H_5$, —$CH_2$—$CH_2$—$C_6H_5$, etc.), and the HX salts thereof, wherein X is a conventional pharmaceutically acceptable acid addition salt anion (e.g., chloride, bromide, perchlorate, methanesulfonate, succinate, etc.);

Further exemplary L-DOPA prodrugs disclosed in U.S. Pat. Nos. 4,065,566 and 4,035,507 include the following:

1. Glycyl-3,4-diacetyloxy-L-phenylalanine and its HX salt, wherein X represents a pharmaceutically acceptable anion.
2. Glycyl-3,4-diacetyloxy-L-phenylalanine-methyl ester and its HX salt, wherein X represents a pharmaceutically acceptable anion.
3. 3,4-diacetyloxy-L-phenylalanyl-glycine and its HX salt, wherein X represents a pharmaceutically acceptable anion.
4. N-nicotinoyl-3,4-dihydroxy-L-phenylalanine and its M salt, wherein M represents an alkali metal.
5. N-nicotinoyl-3,4-diacetyloxy-L-phenylalanine and its M salt, wherein M represents an alkali metal.
6. N-nicotinoyl-3,4-dipivalyloxy-L-phenylalanine and its M salt, wherein M represents an alkali metal.
7. 3,4-diacetyloxy-L-phenylalanyl-glycine and its HX salt, wherein X represents a pharmaceutically acceptable anion.
8. 3,4-diacetyloxy-L-phenylalanyl-glycine-methyl ester and its HX salt, wherein X represents a pharmaceutically acceptable anion.
9. 3,4-diacetyloxy-L-phenylalanyl-glycine-ethyl ester and its HX salt, wherein X represents a pharmaceutically acceptable anion.
10. 3,4-diacetyloxy-L-phenylalanyl-glycine-benzyl ester and its HX salt, wherein X represents a pharmaceutically acceptable anion.
11. 3,4-diacetyloxy-L-phenylalanyl-L-leucine and its HX salt, wherein X represents a pharmaceutically acceptable anion.
12. 3,4-diacetyloxy-L-phenylalanyl-L-leucine-methyl ester and its HX salt, wherein X represents a pharmaceutically acceptable anion.
13. 3,4-diacetyloxy-L-phenylalanyl-L-leucine-ethyl ester and its HX salt, wherein X represents a pharmaceutically acceptable anion.
14. 3,4-diacetyloxy-L-phenylalanyl-L-leucine-benzyl ester and its HX salt, wherein X represents a pharmaceutically acceptable anion.
15. 3,4-diacetyloxy-L-phenylalanyl-L-isoleucine and its HX salt, wherein X represents a pharmaceutically acceptable anion.
16. 3,4-diacetyloxy-L-phenylalanyl-L-isoleucine-methyl ester and its HX salt, wherein X represents a pharmaceutically acceptable anion.
17. 3,4-diacetyloxy-L-phenylalanyl-L-isoleucine-ethyl ester and its HX salt, wherein X represents a pharmaceutically acceptable anion.
18. 3,4-diacetyloxy-L-phenylalanyl-L-isoleucine-benzyl ester and its HX salt, wherein X represents a pharmaceutically acceptable anion.
19. 3,4-diacetyloxy-L-phenylalanyl-phenylalanine and its HX salt, wherein X represents a pharmaceutically acceptable anion.
20. 3,4-diacetyloxy-L-phenylalanyl-phenylalanine-methyl ester and its HX salt, wherein X represents a pharmaceutically acceptable anion.
21. 3,4-diacetyloxy-L-phenylalanyl-phenylalanine-ethyl ester and its HX salt, wherein X represents a pharmaceutically acceptable anion.
22. 3,4-diacetyloxy-L-phenylalanyl-phenylalanine-benzyl ester and its HX salt, wherein X represents a pharmaceutically acceptable anion.
23. Glycyl-3,4-diacetyloxy-L-phenylalanine and its HX salt, wherein X represents a pharmaceutically acceptable anion.
24. Glycyl-3,4-dipivalyloxy-L-phenylalanine and its HX salt, wherein X represents a pharmaceutically acceptable anion.
25. Glycyl-3,4-diacetyloxy-L-phenylalanine-methyl ester and its HX salt, wherein X represents a pharmaceutically acceptable anion.
26. Glycyl-3,4-diacetyloxy-L-phenylalanine-ethyl ester and its HX salt, wherein X represents a pharmaceutically acceptable anion.
27. Glycyl-3,4-diacetyloxy-L-phenylalanine-benzyl ester and its HX salt, wherein X represents a pharmaceutically acceptable anion.
28. L-leucyl-3,4-diacetyloxy-L-phenylalanine and its HX salt, wherein X represents a pharmaceutically acceptable anion.
29. L-leucyl-3,4-diacetyloxy-L-phenylalanine-methyl ester and its HX salt, wherein X represents a pharmaceutically acceptable anion.
30. L-leucyl-3,4-diacetyloxy-L-phenylalanine-ethyl ester and its HX salt, wherein X represents a pharmaceutically acceptable anion.
31. L-leucyl-3,4-diacetyloxy-L-phenylalanine-benzyl ester and its HX salt, wherein X represents a pharmaceutically acceptable anion.
32. L-isoleucyl-3,4-diacetyloxy-L-phenvlalanine and its HX salt, wherein X represents a pharmaceutically acceptable anion.
33. L-isoleucyl-3,4-diacetyloxy-L-phenylalanine-methyl ester and its HX salt, wherein X represents a pharmaceutically acceptable anion.
34. L-isoleucyl-3,4-diacetyloxy-L-phenylalanine-ethyl ester and its HX salt, wherein X represents a pharmaceutically acceptable anion.
35. L-isoleucyl-3,4-diacetyloxy-L-phenylalanine-benzyl ester and its HX salt, wherein X represents a pharmaceutically acceptable anion.
36. Phenylalanyl-3,4-diacetyloxy-L-phenylalanine and its HX salt, wherein X represents a pharmaceutically acceptable anion.
37. Phenylalanyl-3,4-diacetyloxy-L-phenylalanine-methyl ester and its HX salt, wherein X represents a pharmaceutically acceptable anion.
38. Phenylalanyl-3,4-diacetyloxy-L-phenylalanine-ethyl ester and its HX salt, wherein X represents a pharmaceutically acceptable anion.
39. Phenylalanyl-3,4-diacetyloxy-L-phenylalanine-benzyl ester and its HX salt, wherein X represents a pharmaceutically acceptable anion.
40. 3,4-diacetyloxy-L-phenylalanyl-3,4-diacetyloxy-L-phenylalanine and its HX salt, wherein X represents a pharmaceutically acceptable anion.
41. 3,4-diacetyloxy-L-phenylalanyl-3,4-diacetyloxy-L-phenylalanine-methyl ester and its HX salt, wherein X represents a pharmaceutically acceptable anion.

42. 3,4-diacetyloxy-L-phenylalanyl-3,4-diacetyloxy-L-phenylalanine-ethyl ester and its HX salt, wherein X represents a pharmaceutically acceptable anion.
43. 3,4-diacetyloxy-L-phenylalanyl-3,4-diacetyloxy-L-phenylalanine-benzyl ester and its HX salt, wherein X represents a pharmaceutically acceptable anion.
44. N—[N,N-dimethylamino]-glycyl-3,4-diacetyloxy-L-phenylalanine and its M salt, wherein M represents an alkali metal.
45. N-nicotinoyl-3,4-dinicotinoyloxy-L-phenylalanine and its M salt, wherein M represents an alkali metal.
46. N-3-pyridylacetyl-3,4-dihydroxy-L-phenylalanine and its M salt, wherein M represents an alkali metal.
47. N-3-pyridylacetyl-3,4-diacetyloxy-L-phenylalanine and its M salt, wherein M represents an alkali metal.
48. 3,4-N,N-dimethylaminoglycyl-L-phenylalanine methylester and its HX salt, wherein X represents a pharmaceutically acceptable anion.
49. N—[N,N-dimethylamino]glycyl-3,4-[N,N-dimethylaminoglycyl]-L-phenylalanine and its M salt, wherein M represents an alkali metal.
50. N—[N,N-diethylaminoglycyl]-3,4-diacetyloxy-L-phenylalanine and its M salt, wherein M represents an alkali metal.

As used herein, the term "alkyl" refers to a saturated aliphatic hydrocarbon including straight chain and branched chain groups. The alkyl group preferably has between 1 and 30 carbon atoms, more preferably between 1 and 20 carbon atoms. While lower alkyls, e.g., of between 1 and 6 carbon atoms may facilitate the formulation of the compounds, higher alkyls provides for enhanced permeability thereof through the BBB.

The alkyl group, according to the present disclosure, may be substituted or non-substituted. When substituted, the substituent group can be, for example, cycloalkyl, alkenyl, aryl, heteroaryl, heteroalicyclic, hydroxy, alkoxy, aryloxy, thiohydroxy, thioalkoxy, thioaryloxy, halo, carboxy, alkoxycarbonyl, thiocarboxy, carbamyl, and amino, as these terms are defined herein.

As used herein, the term "cycloalkyl" refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane. The cycloalkyl group, according to the present disclosure, may be substituted or non-substituted. When substituted, the substituent group can be, for example, alkyl, cycloalkyl, alkenyl, aryl, heteroaryl, heteroalicyclic, hydroxy, alkoxy, aryloxy, thiohydroxy, thioalkoxy, thioaryloxy, halo, carboxy, alkoxycarbonyl, thiocarboxy, carbamyl, and amino, as these terms are defined herein.

The term "alkenyl" refers to an alkyl group which consists of at least two carbon atoms and at least one carbon-carbon double bond.

The term "alkynyl" refers to an alkyl group which consists of at least two carbon atoms and at least one carbon-carbon triple bond.

As is discussed above, both the alkenyl and the alkynyl groups preferably have between 1 and 30 carbon atoms.

An "aryl" group refers to an all-carbon monocyclic or fused-ring polycyclic (i.e., rings which share adjacent pairs of carbon atoms) group having a completely conjugated pi-electron system. Examples, without limitation, of aryl groups are phenyl, naphthalenyl and anthracenyl. The aryl group, according to the present disclosure, may be substituted or non-substituted. When substituted, the substituent group can be, for example, alkyl, cycloalkyl, alkenyl, aryl, heteroaryl, heteroalicyclic, hydroxy, alkoxy, aryloxy, thiohydroxy, thioalkoxy, thioaryloxy, halo, carboxy, alkoxycarbonyl, thiocarboxy, carbamyl, and amino, as these terms are defined herein.

The term "C-carboxy" refers to a +C(=O)—OR' group, where R' is hydrogen, alkyl, cycloalkyl, alkenyl, aryl, heteroaryl (bonded through a ring carbon) or heteroalicyclic (bonded through a ring carbon) as defined herein.

The term "O-carboxy" refers to a R'—C(=O)—O— group, where R' is hydrogen, alkyl, cycloalkyl, alkenyl, aryl, heteroaryl (bonded through a ring carbon) or heteroalicyclic (bonded through a ring carbon) as defined herein.

The term "carbonyl" refers to a —C(=O)—R' group, where R' is as defined hereinabove.

The term "thiocarbonyl" refers to a —C(=S)—R' group, where R' is as defined hereinabove.

An "O-carbamyl" group refers to an —OC(=O)—NR'R" group, where R' is as defined hereinabove and R" is as defined for R'.

An "O-thiocarbamyl" group refers to an —OC(=S)—NR'R" group, where R' is and R" are as defined hereinabove.

A "fatty acid acyl" refers to a R'''C(=O)—O— group, where R''' is a saturated or unsaturated hydrocarbon chain having at least 10 carbon atoms.

The term "alkoxy" refers to both an —O-alkyl and an —O-cycloalkyl group, as defined hereinabove. Representative examples of alkoxy groups include methoxy, ethoxy, propoxy and tert-butoxy.

The —O-alkyl and the O-cycloalkyl groups, according to the present disclosure, may be substituted or non-substituted. When substituted, the substituent group can be, for example, cycloalkyl, alkenyl, aryl, heteroaryl, heteroalicyclic, hydroxy, alkoxy, aryloxy, thiohydroxy, thioalkoxy, thioaryloxy, halo, carboxy, alkoxycarbonyl, thiocarboxy, carbamyl, and amino, as these terms are defined herein.

The term "thioalkoxy" refers to both an —S-alkyl group, and an —S-cycloalkyl group, as defined herein.

The term "hydroxy" refers to an —OH group.

The term "thiohydroxy" refers to an —SH group.

An "aryloxy" group refers to both an —O-aryl and an —O-heteroaryl group, as defined herein.

A "thioaryloxy" group refers to both an —S-aryl and an —S-heteroaryl group, as defined herein.

The term "amino" refers to a —NR'R" group, with R' and R" as defined hereinabove.

The term "alkoxycarbonyl", which is also referred to herein interchangeably as "carbalkoxy" refers to a carboxy group, as defined hereinabove, where R' is not hydrogen.

The term "heteroaryl" group includes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system.

The term "halo" refers to a fluorine, chlorine, bromine or iodine atom.

The term "phosphonyl" describes an —P(=O)(OR')$_2$ group, with R' as defined hereinabove.

In any embodiment of the compositions of the disclosure, the composition may comprise both L-DOPA and one or more L-DOPA prodrugs, or pharmaceutically acceptable salts thereof In a further embodiment, the composition further comprises carbidopa or pharmaceutically acceptable salt thereof. In this embodiment, the carbidopa or pharmaceutically acceptable salt thereof may be present in the same dosage form as the other active components, or may be provided as a separate component, such as a separate dosage form provided in a kit or blister pack with the other component(s)

The compositions of the disclosure may be provided in the form of pharmaceutical or nutraceutical compositions including one or more non-toxic acceptable carriers and/or diluents and/or adjuvants, and if desired other active ingredients. The compositions may be made up in a solid form (including granules, powders or suppositories) or in a liquid form (e.g., solutions, suspensions, or emulsions). The compositions may be provided in a variety of solutions and may be subjected to conventional operations such as sterilization and/or may contain conventional adjuvants, such as preservatives, stabilizers, wetting agents, emulsifiers, buffers etc.

The compositions may be formulated for administration by any suitable route, including but not limited to oral, topical (including but not limited to eye drops and ophthalmic ointments), parenteral, intranasal, pulmonary, or rectal in dosage unit formulations containing conventional non-toxic acceptable carriers, adjuvants and vehicles.

In one embodiment the compositions may be in a form suitable for oral use, for example, as tablets, troches, lozenges, aqueous or oily suspensions, dispersible powders or granules, emulsion, hard or soft capsules, or syrups or elixirs.

In another embodiment the compositions are formulated as eye drops. Eye drops can be prepared using techniques including but not limited to, using a tonicity agent such as sodium chloride or concentrated glycerin, a buffer such as sodium phosphate or sodium acetate, a surfactant such as polyoxyethylene sorbitan monooleate, polyoxyl 40 stearate or polyoxyethylene hydrogenated castor oil, a stabilizer such as sodium citrate or sodium edetate, a preservative such as benzalkonium chloride or paraben as needed. The pH of the eye drops is preferably in the range of from 4 to 8. Ophthalmic ointments can be prepared with a generally used base such as white soft paraffin or liquid paraffin.

Compositions formulated for oral use may contain one or more agents selected from the group consisting of sweetening agents, flavoring agents, coloring agents and preservative agents in order to provide palatable preparations. The tablets may contain the compositions in admixture with non-toxic acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated. In some cases such coatings may be prepared to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the composition is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions may contain the composition in admixture with excipients suitable for the manufacture of aqueous suspensions. Such excipients may include suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the compositions in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water may provide the composition in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

The compositions may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In one embodiment, the compositions comprise a dosage form, and the dosage forms may include any suitable amount of each L-DOPA, melatonin, analogues thereof, or pharmaceutically acceptable salts thereof as deemed appropriate by attending medical personnel based on, for example, the choice of the compound, the planned route of administration, the nature of the formulation, the nature of the subject's condition, and the judgment of the attending practitioner.

In various non-limiting embodiments, L-DOPA and/or L-DOPA analogues may be administered at dosages of between 1 μg and 6000 mg/day; between 1 μg and 3000 mg/day; between 1 μg and 1000 mg/day; 5 μg and 6000 mg/day; between 5 μg and 3000 mg/day; between 5 μg and 1000 mg/day; between 50 μg and 6000 mg/day; between 50 μg and 3000 mg/day: between 50 μg and 1000 mg/day: between 100 μg and 6000 mg/day; between 100 μg and 3000 mg/day: between 100 μg and 1000 mg/day; between 500 μg and 6000 mg/day; between 500 μg and 3000 mg/day; between 500 μg and 1000 mg/day: between 1 mg and 6000 mg/day; between 1 mg and 3000 mg/day; between 1 mg and 1000 mg/day; between 10 mg/day and 6000 mg/day, between 10 mg/day and 3000 mg/day, between 50 mg/day and 6000 mg/day, between 50 mg/day and 3000 mg/day, between 50 mg/day and 1000 mg/day, between 100 mg/day and 6000 mg/day, between 100 mg/day and 3000 mg/day, between 100 mg/day and 1000 mg/day, between 250 mg/day and 6000 mg/day, between 250 mg/day and 3000 mg/day, between 250 mg/day and 1000 mg/day, between 500 mg/day and 6000 mg/day, between 500 mg/day and 3000 mg/day, or between 500 mg/day and 1000 mg/day. Thus, the dosage forms may be provided to most appropriately deliver this dosage form to a subject.

In various non-limiting embodiments, melatonin and/or melatonin analogues may be administered at dosages of between 1 μg and 40 mg/day; between 1 μg and 20 mg/day; between 1 μg and 10 mg/day: 5 μg and 40 mg/day: between 5 μg and 20 mg/day: between 5 μg and 10 mg/day: between 50 μg and 40 mg/day: between 50 μg and 20 mg/day: between 50 μg and 10 mg/day; between 100 μg and 40 mg/day; between 100 μg and 20 mg/day; between 100 μg and 10 mg/day; between 500 μg and 40 mg/day; between 500 μg and 20 mg/day; between 500 μg and 10 mg/day: between 1 mg/day and 40 mg/day, 1 mg/day and 30 mg/day, 1 mg/day and 20 mg/day, 1 mg/day and 10 mg/day, 1 mg/day and 5 mg/day, 3 mg/day and 40 mg/day, 3 mg/day and 30 mg/day, 3 mg/day and 20 mg/day, 3 mg/day and 10 mg/day, 3 mg/day and 5 mg/day, 5 mg/day and 40 mg/day, 5 mg/day and 30 mg/day, 5 mg/day and 20 mg/day, 5 mg/day and 10 mg/day, 10 mg/day and 40 mg/day, 10 mg/day and 30 mg/day, or 10 mg/day and 20 mg/day. Thus, the dosage forms may be provided to most appropriately deliver this dosage form to a subject. However, it will be understood that the amount of the compounds actually administered will be determined by a physician, in the light of the above relevant circumstances. Therefore, the above dosage ranges are not intended to limit the scope of the disclosure in any way.

In a second aspect, the disclosure provides methods for treating or limiting development of AMD, comprising administering to a subject in need thereof an amount effective to treat or limit development of AMD of:

(a) a GPR143 agonist; and
(b) melatonin, a melatonin analogue, or a pharmaceutically acceptable salt thereof.

In one embodiment, the GPR143 agonist comprises L-DOPA, an L-DOPA analogue, or a pharmaceutically acceptable salt thereof.

As shown in the examples that follow, the inventors have demonstrated that circadian agents alter retinal pigment epithelial (RPE) cell VEGF expression in a rhythmic manner, with dopamine receptors increasing RPE VEGF secretion, while melatonin and a GPR143 agonist exemplified by L-DOPA antagonize dopamine effects, and thus that combining GPR 143 agonists and melatonin or melatonin analogues induce RPE cells into a circadian rhythm that controls VEGF expression (a key contributor to AMD development).

In a further embodiment, the method further comprises administering carbidopa or a pharmaceutically acceptable salt thereof.

Thus, in various on-limiting embodiments, the administering is done in the evening 2 hours (120 minutes) or less before the subject goes to bed, 90 minutes or less before the subject goes to bed, 1 hour (60 minutes) or less before the subject goes to bed, 45 minutes or less before the subject goes to bed, 30 minutes or less before the subject goes to bed, 15 minutes or less before the subject goes to bed, or just before the subject goes to bed. In a further embodiment, the administering is done once per day (such as in the evening 2 hours or less before the subject goes to bed), though the administering may be done at any suitable time interval as determined by attending medical personnel, including but not limited to twice per day, once per day, once every two days, once every three, days, etc.

In a further embodiment, the administering is done in the evening 2 hours (120 minutes) or less before sunset, 90 minutes or less before sunset, 1 hour (60 minutes) or less before sunset, 45 minutes or less before sunset, 30 minutes or less before sunset, or 15 minutes or less before sunset. In a further embodiment, the administering is done once per day, though the administering may be done at any suitable time interval as determined by attending medical personnel, including but not limited to twice per day, once per day, once every two days, once every three, days, etc.

In one embodiment the L-DOPA and/or L-DOPA analogue, and the melatonin, melatonin analogue, and/or (when administered) the carbidopa, or pharmaceutically acceptable salts thereof, are administered separately to the subject, as independent dosage forms. The L-DOPA and/or L-DOPA analogue, and the melatonin, and/or melatonin analogue may include any suitable such compound, including but not limited to those described above in the first aspect of the disclosure. In another embodiment, the L-DOPA and/or L-DOPA analogue, and the melatonin, melatonin analogue, are administered together, such as in a combined dosage form or nutraceutical. In a further embodiment, the dosage form administered may further include carbidopa or pharmaceutically acceptable salt thereof, or the carbidopa or pharmaceutically acceptable salt thereof nay be administered separately. In one embodiment, the L-DOPA and/or L-DOPA analogue, and the melatonin, melatonin analogue, and (when administered) the carbidopa, or pharmaceutically acceptable salts thereof, are administered together as the composition of any embodiment or combination of embodiments of the first aspect of the disclosure.

The subject may be any subject that may suitably be treated for AMD or to limit development of AMD. In one embodiment, the subject is a mammal, including but not limited to a human.

As used herein for all aspects and embodiments of the disclosure. "AMD" means an aging-associated disease resulting in the loss of vision in the macula (the center of the visual field) because of damage to the retina know as Age-related Macular Degeneration. As used herein, AMD encompasses both wet and dry AMD, described in more detail below.

AMD begins with characteristic drusen (yellow deposits) in the macula between the retinal pigment epithelium and the underlying choroid. Most people with these early changes (referred to as age-related maculopathy) have good vision. People with drusen can go on to develop advanced AMD. The risk is considerably higher when the drusen are large and numerous and associated with disturbance in the pigmented cell layer under the macula. A second type of material shown to accumulate in AMD is lipofucsin. It is seen by autofluorescence photography of patients with AMD and is most prominent at the leading edge of RPE cell loss otherwise known as geographic atrophy. It is believed to be a complex mixture of undigested, oxidized photoreceptor outer segment derivatives trapped in RPE lysosomes. In turn the immune system is thought to clear this material and in doing so destroys the RPE and overlying retina resulting in an area of atrophy or GA. Lipofuscin accumulation is a major risk factor for vision loss and progression of age-related macular degeneration. More recently a third material, reticular pseudodrusen (RPD), has been observed on OCT scans of patients with AMD. The RPD appear between the apical surface of the RPE and photoreceptor. The composition of this material may consist of incompletely processed outer segment (OS) that are normally metabolized by the RPE in a controlled fashion aligned with the circadian rhythm. These RPD also put individuals at increased risk for GA and wet AMD. As used herein. GA" mean "geographic atrophy", is a chronic progressive degeneration of the macula, as part of late-stage AMD. GA is characterized by localized atrophy of retinal tissue and choriocapillaris, leading to central scotomas and permanent loss of visual acuity.

Subjects with age-related maculopathy may progress to either of the two main forms of advanced AMD, each of which can be treated or be limited in its development using the methods of the disclosure. 'Wet' AMD causes vision loss due to abnormal blood vessel growth that begins in the choriocapillaries and the new vessels, blood, or serous fluid may accumulate under the retina or break through Bruch's membrane into the retina and the macula. Bleeding, leaking, and scarring from these blood vessels eventually causes irreversible damage to the photoreceptors and rapid vision loss if left untreated. Blurring in intermediate AMD may be due to the accumulation of drusen under the retinal pigment epithelium (RPE) which alters to focal properties of the photoreceptors by moving them out of the plane of focus.

Dry AMD may occur in one or both eyes, and can advance from age-related maculopathy into intermediate or advanced stages of dry AMD:

Intermediate Dry AMD: Either many medium-sized drusen or one or more large drusen. Some people see a blurred spot in the center of their vision. More light may be needed for reading and other tasks.

Advanced Dry AMD: In addition to drusen, a breakdown of light-sensitive cells and/or RPE and supporting tissue in the central retinal area. This breakdown can cause a blurred spot in the center of vision. Over time, the blurred spot may get bigger and darker, taking more of the central vision; may have difficulty reading or recognizing faces until they are very close to you.

AMD symptoms include, but are not limited to blurred/reduced central vision, central scotomas (shadows or missing areas of vision), trouble discerning one dark color from another dark color and/or one light color from another light color; slow recovery of visual function after exposure to bright light, a loss in contrast sensitivity, so that contours, shadows and color vision are less vivid, retinal pigment epithelial (RPE) disturbance (including pigment clumping and/or dropout), RPE detachment, geographic atrophy, subretinal neovascularization, and disciform scar, and distorted vision (metamorphopsia), such that a grid of straight lines appears wavy and parts of the grid may appear blank. Symptoms of dry AMD and wet AMD are generally similar early during disease progression, and thus it may not be possible to determine which early-stage patients will develop dry vs. wet forms of AMD. Dry AMD may develop as 'geographic atrophy', and early AMD become 'wet' AMD when new blood vessels sprout.

As used herein, "treat" or "treating" AMD means accomplishing one or more of the following: (a) reducing the severity of AMD such as size and number of drusen or RPD; (b) limiting or preventing development of one or more symptoms characteristic of AMD, as described above, including but not limited to vision loss; (c) inhibiting worsening of one or more symptoms characteristic of AMD, as described above, including but not limited to vision loss; (d) limiting or preventing recurrence of AMD in patients that have previously had the disorder(s); (e) limiting or preventing recurrence of one or more symptoms in patients that were previously symptomatic for AMD, (f) limiting progression of age-related maculopathy to AMD (wet or dry), or intermediate dry AMD to advanced dry or GA or 'wet' AMD or arresting the progression of GA or wet AMD, and/or improving health of the aging eyes or eyes with AMD. Such treating includes treating of dry AMD, advanced dry AMD or GA, and/or wet AMD.

In one embodiment, the subject is undergoing anti-vascular endothelial growth factor therapy.

As used herein, the term "limiting development of" AMD means to prevent or to minimize development of AMD in individuals at risk of developing AMD. In one preferred embodiment, the methods comprise treating a subject with drusen accumulation (ie: age-related maculopathy), to limit development of AMD. In another preferred embodiment, the methods comprise treating a subject with an amount effective of the GPR143 agonist to decrease the rate of lines of loss of vision relative to a non-treated AMD subject, or subject at risk of AMD. In another preferred embodiment, the methods comprise treating a subject with wet AMD, or at risk of developing wet AMD, an amount effective of the GPR143 agonist to decrease the rate and number of new blood vessel formation. As discussed in more detail below, GPR143 stimulation causes the RPE to increase PEDF secretion, and PEDF is a potent anti-angiogenic factor. Thus, GPR143 stimulation may stop new blood vessel development in 'wet' AMD, in addition to its effects on retinal development discussed herein In another preferred embodiment, the methods comprise treating a subject that has blurred or reduced central vision with an amount of GPR143 agonist effective to increase the lines of visual acuity in one or both eyes. In this embodiment, the lines of visual acuity are as measured by the standard Snellen test, where the increase or decrease in 'lines' of visual acuity are based on which smallest 'line' on a Snellen chart a patient can read clearly.

"Subjects at risk of developing AMD" mean anyone with any risk factor for development of AMD, including but not limited to being over 50 years old (in various preferred embodiments, over 60 years old, over 65 years old, over 70 years old, or over 75 years old), presence of drusen deposits, presence of lipofuscin, presence of pseudodrusen (RPD), Caucasian race, whites, having a blood relative that has or had AMD, a mutation in the complement factor H gene (CFH) of (Tyr402His), Arg80Gly variant of the complement protein C3 gene, hypertension, high cholesterol levels, obesity, smoking, a high fat intake, and mutations in the fibulin 5 gene. Thus, in a preferred embodiment, the subject to be treated has one or more of these risk factors, particularly in methods for limiting development of AMD.

The L-DOPA and/or L-DOPA analogue, and the melatonin, melatonin analogue, and (when administered) the carbidopa, or pharmaceutically acceptable salts thereof, are administered in an amount sufficient to carry out the methods of the disclosure. Amounts effective for these uses depend on factors including, but not limited to, the nature of the compound (specific activity, etc.), the route of administration, the stage and severity of the disorder, the weight and general state of health of the subject, and the judgment of the prescribing physician. The active compounds are effective over a wide dosage range. In various non-limiting embodiments, L-DOPA and/or L-DOPA analogues may be administered at dosages of between 1 µg and 6000 mg/day: between 1 µg and 3000 mg/day; between 1 µg and 1000 mg/day; 5 µg and 6000 mg/day; between 5 µg and 3000 mg/day; between 5 µg and 1000 mg/day: between 50 µg and 6000 mg/day; between 50 µg and 3000 mg/day; between 50 µg and 1000 mg/day; between 100 µg and 6000 mg/day; between 100 µg and 3000 mg/day; between 100 µg and 1000 mg/day; between 500 µg and 6000 mg/day: between 500 µg and 3000 mg/day; between 500 µg and 1000 mg/day; between 1 mg and 6000 mg/day; between 1 mg and 3000 mg/day; between 1 mg and 1000 mg/day: between 10 mg/day and 6000 mg/day, between 10 mg/day and 3000 mg/day, between 50 mg/day and 6000 mg/day, between 50 mg/day and 3000 mg/day, between 50 mg/day and 1000 mg/day, between 100 mg/day and 6000 mg/day, between 100 mg/day and 3000 mg/day, between 100 mg/day and 1000 mg/day, between 250 mg/day and 6000 mg/day, between 250 mg/day and 3000 mg/day, between 250 mg/day and 1000 mg/day, between 500 mg/day and 6000 mg/day, between 500 mg/day and 3000 mg/day, or between 500 mg/day and 1000 mg/day. Thus, the dosage forms may be provided to most appropriately deliver this dosage form to a subject.

In various non-limiting embodiments, melatonin and/or melatonin analogues may be administered at dosages of between 1 µg and 40 mg/day; between 1 µg and 20 mg/day; between 1 µg and 10 mg/day; between 5 µg and 40 mg/day; between 5 µg and 20 mg/day; between 5 µg and 10 mg/day; between 50 µg and 40 mg/day; between 50 µg and 20 mg/day; between 50 µg and 10 mg/day: between 100 µg and 40 mg/day; between 100 µg and 20 mg/day: between 100 µg and 10 mg/day: between 500 µg and 40 mg/day; between 500 µg and 20 mg/day; between 500 µg and 10 mg/day; between 1 mg/day and 40 mg/day, 1 mg/day and 30 mg/day, 1 mg/day and 20 mg/day, 1 mg/day and 10 mg/day, 1 mg/day and 5 mg/day, 3 mg/day and 40 mg/day, 3 mg/day and 30 mg/day, 3 mg/day and 20 mg/day, 3 mg/day and 10 mg/day, 3 mg/day and 5 mg/day, 5 mg/day and 40 mg/day, 5 mg/day and 30 mg/day, 5 mg/day and 20 mg/day, 5 mg/day and 10 mg/day, 10 mg/day and 40 mg/day, 10 mg/day and 30 mg/day, or 10 mg/day and 20 mg/day. However, it will be understood that the amount of the compounds actually administered will be determined by a physician, in the light of the above relevant circumstances. Therefore, the above dosage ranges are not intended to limit the scope of the disclosure in any way.

The L-DOPA and/or L-DOPA analogue, and the melatonin, and/or melatonin analogues may be the sole therapeutic compounds administered, or they may be administered with one or more additional therapeutic treatments. In one embodiment, the methods may further comprise administering a further therapeutic compound to the subject, including but not limited to an L-amino acid decarboxylase inhibitor, such as carbidopa (which may be increased from the usual 25 mg to reduce toxicity/symptoms) or benserazide. Such L-amino acid decarboxylase inhibitors can be used, for example, to increase plasma half-life of L-DOPA and reduce conversion of L-DOPA to dopamine peripherally, which reduces side effects of L-DOPA treatment. In another embodiment, the methods may further comprise administering one or more other compounds useful for treating or limiting development of AMD, including but not limited to anti-angiogenic therapeutics, such as anti-vascular endothelial growth factor (VEGF) agents, including but not limited to VEGF antibodies (or fragments thereof) such as ranibizumab or bevacizumab, or VEGF aptamers, such as pegaptanib. When administered as a combination, combination can be formulated as separate compositions that are given at the same time or different times, or can be given as a single composition.

In another embodiment, the methods may further comprise light therapy, such as light therapy administered to the subject in the morning after receiving the therapeutic methods disclosed herein in the evening, such as 2 hours or less before the subject goes to bed.

The dosage of each L-DOPA, melatonin, analogues thereof, and (when administered) the carbidopa, or pharmaceutically acceptable salts thereof depends on the choice of the compound, the route of administration, the nature of the formulation, the nature of the subject's condition, and the judgment of the attending practitioner. In various non-limiting embodiments, L-DOPA and/or L-DOPA analogues may be administered at dosages of between 1 µg and 6000 mg/day: between 1 µg and 3000 mg/day; between 1 µg and 1000 mg/day; between 5 µg and 6000 mg/day; between 5 µg and 3000 mg/day; between 5 µg and 1000 mg/day; between 50 µg and 6000 mg/day; between 50 µg and 3000 mg/day; between 50 µg and 1000 mg/day: between 100 µg and 6000 mg/day; between 100 µg and 3000 mg/day; between 100 µg and 1000 mg/day; between 500 µg and 6000 mg/day: between 500 µg and 3000 mg/day; between 500 µg and 1000 mg/day; between 1 mg and 6000 mg/day; between 1 mg and 3000 mg/day; between 1 mg and 1000 mg/day; between 10 mg/day and 6000 mg/day, between 10 mg/day and 3000 mg/day, between 50 mg/day and 6000 mg/day, between 50 mg/day and 3000 mg/day, between 50 mg/day and 1000 mg/day, between 100 mg/day and 6000 mg/day, between 100 mg/day and 3000 mg/day, between 100 mg/day and 1000 mg/day, between 250 mg/day and 6000 mg/day, between 250 mg/day and 3000 mg/day, between 250 mg/day and 1000 mg/day, between 500 mg/day and 6000 mg/day, between 500 mg/day and 3000 mg/day, or between 500 mg/day and 1000 mg/day. In various non-limiting embodiments, melatonin and/or melatonin analogues may be administered at dosages of between 1 µg and 40 mg/day; between 1 µg and 20 mg/day; between 1 µg and 10 mg/day;

between 5 µg and 40 mg/day; between 5 µg and 20 mg/day; between 5 µg and 10 mg/day; between 50 µg and 40 mg/day: between 50 µg and 20 mg/day: between 50 µg and 10 mg/day; between 100 µg and 40 mg/day; between 100 µg and 20 mg/day; between 100 µg and 10 mg/day; between 500 µg and 40 mg/day; between 500 µg and 20 mg/day: between 500 µg and 10 mg/day: between 1 mg/day and 40 mg/day, 1 mg/day and 30 mg/day, 1 mg/day and 20 mg/day, 1 mg/day and 10 mg/day, 1 mg/day and 5 mg/day, 3 mg/day and 40 mg/day, 3 mg/day and 30 mg/day, 3 mg/day and 20 mg/day, 3 mg/day and 10 mg/day, 3 mg/day and 5 mg/day, 5 mg/day and 40 mg/day, 5 mg/day and 30 mg/day, 5 mg/day and 20 mg/day, 5 mg/day and 10 mg/day, 10 mg/day and 40 mg/day, 10 mg/day and 30 mg/day, or 10 mg/day and 20 mg/day.

The therapeutic compounds may be administered by any suitable route, including but not limited to oral, topical (including but not limited to eye drops and ophthalmic ointments), parenteral, intranasal, pulmonary, or rectal in dosage unit formulations containing conventional non-toxic pharmaceutically acceptable carriers, adjuvants and vehicles, as described above.

Examples

Circadian Patterns of Secretion of VEGF by RPE;

The purpose of this study was to test whether retinal pigment epithelium (RPE) cells express vascular endothelial growth factor (VEGF) in a circadian manner. We tested the hypothesis that 12 hour alternating intervals of dopamine then melatonin combined with L-DOPA would induce RPE cells into a circadian rhythm that controlled VEGF expression. Methods: RPE monolayers were produced on snap-well filters, which were maintained in static culture conditions for at least six months, during which time they became pigmented and well differentiated. We used a continuous perfusion system thereafter, and collected separate apical and basal effluents every 2 hours. A baseline of VEGF secretion was established over a 3-week period. After the baseline was established, the cells were perfused with media containing 1 µM dopamine for 12 hours, then media containing 1 µM melatonin plus 1 µM L-DOPA for the next 12 hours. In this perfusion system, the drug concentrations began at zero, and gradually increased to the full concentration over 12 hours, when the next drug was begun. Initiation of the next drug dilutes the previous over 12 hours while simultaneously ramping up the new drug. Cells were maintained in this circadian rhythm for at least three cycles. Samples were collected at 2-hour intervals and VEGF was quantified via ELISA. The amount of VEGF was plotted against the time of perfusion and fitted using the Cosinor method to find a length of circadian cycle and corresponding p-value for statistical analysis.

Figure 1A:
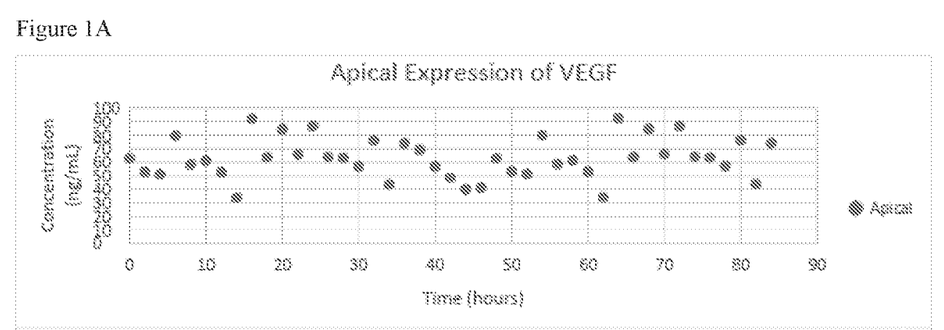
FIG. 1A-1B. Graphs showing expression of VEGF from retinal pigment epithelial (RPE) cells from apical (FIG. 1A) and basal (FIG. 1B) secretion, after RPE cells were perfused with 12-hour intervals of dopamine then melatonin/L-DOPA.
Figure 1B:
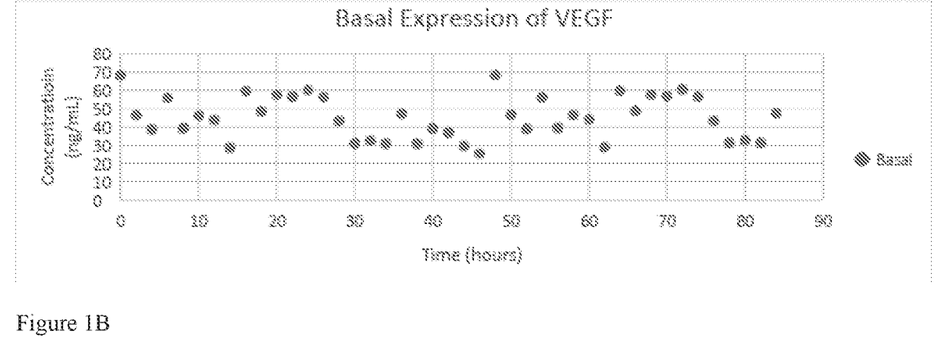

Results: The baseline expression of VEGF in the perfusion system was below the limit of detection prior to addition of the circadian drugs. When the cells were perfused with the 12-hour intervals of dopamine then melatonin/L-DOPA, the amount of VEGF expressed showed a circadian cycle of 23.5 hours (p<0.05) for the basal secretion (see FIG. 1B), but only 16.1 hours (p<0.05) for the apical side of the cells (see FIG. 1A). The difference between the apical and basal periodicity is attributable to the volume and exchange rate differences between the apical and basal chambers. Apical volume was 4.4 ml while the basal volume was 1.76 ml, but we collected 575 µ/hr from each side.

Conclusion: Our results show that circadian agents can alter RPE VEGF expression in a rhythmic manner, and indicate that dopamine receptors increase RPE VEGF secretion, while melatonin and L-DOPA antagonize dopamine effects.

We claim:

1. A method for treating or limiting development of age-related macular degeneration (AMD), comprising administering orally, topically to the eyes, or intranasally, in the evening, to a subject in need thereof an amount effective to treat or limit development of AMD of
    (a) a GPR143 receptor agonist selected from the group consisting of L-DOPA, an L-DOPA analogue, and pharmaceutically acceptable salts thereof; and
    (b) melatonin, a melatonin analogue selected from the group consisting of ramelteon, agomelatine and tasimelteon, or a pharmaceutically acceptable salt thereof.

2. The method of claim 1, wherein the GPR143 receptor agonist is selected from the group consisting of L-DOPA and-pharmaceutically acceptable salts thereof.

3. The method of claim 1, wherein the administering is done in the evening two hours or less before the subject goes to bed.

4. The method of claim 1, wherein the administering comprises oral administering.

5. The method of claim 1, wherein the administering comprises administering by eye drops.

6. The method of claim 1, wherein the administering comprises intranasal administering.

7. The method of claim 1, wherein the method is for treating a subject with wet acute macular degeneration (AMD).

8. The method of claim 1, wherein the method is for treating a subject with dry AMD.

9. The method of claim 1, wherein the subject is undergoing anti-vascular endothelial growth factor therapy.

10. The method of claim 1, wherein the subject has one or more of drusen deposits, lipofuscin deposits, or pseudodrusen (RPD) deposits.

11. The method of claim 1, wherein the method further comprises treating the subject with light therapy.

12. The method of claim 1, wherein the L-DOPA is in a form selected from the group consisting of L-DOPA esters and bile acid conjugates of L-DOPA.

13. The method of claim 1, comprising administering to a subject in need thereof an amount effective to treat or limit development of AMD of:
    (a) between 100 and 300 mg L-DOPA or a pharmaceutically acceptable salt thereof; and
    (b) melatonin or a pharmaceutically acceptable salt thereof.

14. The method of claim 1 comprising wherein the L-DOPA is administered in a dosage of 100 mg L-DOPA/day.

15. The method of claim 1 wherein the melatonin is administered in a dosage of between 1 and 10 mg melatonin/day.

16. The method of claim 1 wherein the GPR143 receptor agonist and the melatonin are administered once every two or three days.

17. The method of claim 15 wherein the melatonin is administered in a dosage of between 5 and 10 mg melatonin/day.

* * * * *